(12) United States Patent
Sherburne

(10) Patent No.: US 8,470,016 B2
(45) Date of Patent: *Jun. 25, 2013

(54) STENT AND OTHER OBJECT REMOVAL FROM A BODY

(75) Inventor: Paul Stevenson Sherburne, Minneapolis, MN (US)

(73) Assignee: Paul Sherburne, Minneapolis, MN (US)

( * ) Notice: Subject to any disclaimer, the term of this patent is extended or adjusted under 35 U.S.C. 154(b) by 123 days.

This patent is subject to a terminal disclaimer.

(21) Appl. No.: 13/200,301

(22) Filed: Sep. 22, 2011

(65) Prior Publication Data

US 2012/0016455 A1    Jan. 19, 2012

Related U.S. Application Data

(63) Continuation of application No. 11/190,797, filed on Jul. 27, 2005, now Pat. No. 8,038,704.

(51) Int. Cl.
*A61F 2/84* (2006.01)

(52) U.S. Cl.
USPC ............................ 623/1.11; 606/108; 606/194

(58) Field of Classification Search
USPC ..... 606/108, 191, 192, 194, 200; 604/103.07, 604/916; 623/1.11, 1.12, 1.23
See application file for complete search history.

(56) References Cited

U.S. PATENT DOCUMENTS

| | | |
|---|---|---|
| 3,831,587 A | 8/1974 | Boyd |
| 4,469,100 A | 9/1984 | Hardwick |
| 4,990,151 A | 2/1991 | Wallsten |
| 5,334,208 A | 8/1994 | Soehendra et al. |
| 5,409,495 A | 4/1995 | Osborn |
| 5,411,507 A | 5/1995 | Heckele |
| 5,411,549 A | 5/1995 | Peters |
| 5,445,646 A | 8/1995 | Euteneuer et al. |
| 5,464,408 A | 11/1995 | Duc |
| 5,474,563 A | 12/1995 | Myler et al. |
| 5,520,697 A | 5/1996 | Lindenberg et al. |
| 5,549,615 A | 8/1996 | Hocherl et al. |
| 5,624,450 A | 4/1997 | Glastra |
| 5,628,754 A | 5/1997 | Shevlin et al. |
| 5,643,277 A | 7/1997 | Soehendra et al. |
| 5,643,309 A | 7/1997 | Myler et al. |
| 5,649,906 A | 7/1997 | Gory et al. |
| 5,653,684 A | 8/1997 | Laptewicz et al. |
| 5,662,703 A | 9/1997 | Yurek et al. |
| 5,681,345 A | 10/1997 | Euteneuer |
| 5,683,451 A | 11/1997 | Lenker et al. |
| 5,690,644 A | 11/1997 | Yurek et al. |
| 5,713,948 A | 2/1998 | Uflacker |
| 5,716,410 A | 2/1998 | Wang et al. |
| 5,733,302 A | 3/1998 | Myler et al. |
| 5,776,186 A | 7/1998 | Uflacker |
| 5,785,715 A | 7/1998 | Schatz |
| 5,788,707 A | 8/1998 | Del Toro et al. |

(Continued)

*Primary Examiner* — Ryan Severson

(57) ABSTRACT

This disclosure contains methods, devices, and systems for object removal from a body, including removal of a stent from a body. Some methods of the present disclosure include inflating a balloon on a catheter, engaging a stent with a socket defined by a surface of the balloon, the surface inwardly sloped toward a lumen of the catheter, and retracting a portion of the stent through the socket and into the lumen. The present disclosure also includes methods for making a catheter, including forming a balloon, inverting a portion of the balloon, and attaching the balloon to a catheter such that a surface of the balloon defines a socket that is inwardly sloped toward a lumen of the catheter.

20 Claims, 8 Drawing Sheets

U.S. PATENT DOCUMENTS

| | | | |
|---|---|---|---|
| 5,833,707 | A | 11/1998 | Mcintyre et al. |
| 5,848,964 | A | 12/1998 | Samuels |
| 5,868,753 | A | 2/1999 | Schatz |
| 5,882,335 | A | 3/1999 | Leone et al. |
| 5,910,144 | A | 6/1999 | Hayashi |
| 5,941,895 | A | 8/1999 | Myler et al. |
| 5,976,172 | A | 11/1999 | Homsma et al. |
| 6,019,779 | A | 2/2000 | Thorud et al. |
| 6,027,508 | A | 2/2000 | Ren et al. |
| 6,039,721 | A | 3/2000 | Johnson et al. |
| 6,059,813 | A | 5/2000 | Vrba et al. |
| 6,066,155 | A | 5/2000 | Amann et al. |
| 6,077,298 | A | 6/2000 | Tu et al. |
| 6,106,531 | A | 8/2000 | Schatz |
| 6,146,389 | A | 11/2000 | Geitz |
| 6,187,016 | B1 | 2/2001 | Hedges et al. |
| 6,221,096 | B1 | 4/2001 | Aiba et al. |
| 6,221,097 | B1 | 4/2001 | Wang et al. |
| 6,258,098 | B1 | 7/2001 | Taylor et al. |
| 6,280,464 | B1 * | 8/2001 | Hayashi ................ 623/1.11 |
| 6,283,959 | B1 | 9/2001 | Lalonde et al. |
| 6,319,251 | B1 | 11/2001 | Tu et al. |
| 6,325,818 | B1 | 12/2001 | Werneth |
| 6,331,186 | B1 | 12/2001 | Wang et al. |
| 6,350,277 | B1 | 2/2002 | Kocur |
| 6,358,276 | B1 | 3/2002 | Edwin |
| 6,478,814 | B2 | 11/2002 | Wang et al. |
| 6,569,181 | B1 | 5/2003 | Burns |
| 6,576,005 | B1 | 6/2003 | Geitz |
| 6,579,305 | B1 | 6/2003 | Lashinski |
| 6,582,396 | B1 | 6/2003 | Parodi |
| 6,613,075 | B1 | 9/2003 | Healy et al. |
| 6,645,222 | B1 | 11/2003 | Parodi et al. |
| 6,663,651 | B2 | 12/2003 | Krolik et al. |
| 6,676,692 | B2 | 1/2004 | Rabkin et al. |
| 6,802,846 | B2 | 10/2004 | Hauschild et al. |
| 6,837,901 | B2 | 1/2005 | Rabkin et al. |
| 6,939,370 | B2 | 9/2005 | Hartley et al. |
| 6,942,682 | B2 | 9/2005 | Vrba et al. |
| 6,945,990 | B2 | 9/2005 | Greenan |
| 7,096,554 | B2 | 8/2006 | Austin et al. |
| 7,153,320 | B2 | 12/2006 | Euteneuer et al. |
| 7,198,636 | B2 | 4/2007 | Cully et al. |
| 7,241,257 | B1 | 7/2007 | Ainsworth et al. |
| 7,556,641 | B2 | 7/2009 | Cully et al. |
| 7,608,099 | B2 | 10/2009 | Johnson et al. |
| 7,753,945 | B2 | 7/2010 | Bruun et al. |
| 7,828,766 | B2 | 11/2010 | Durcan |
| 7,833,262 | B2 | 11/2010 | McGuckin, Jr. et al. |
| 7,837,720 | B2 | 11/2010 | Mon |
| 2001/0011179 | A1 | 8/2001 | Adams |
| 2002/0026230 | A1 | 2/2002 | Moll et al. |
| 2002/0120277 | A1 | 8/2002 | Hauschild et al. |
| 2003/0023204 | A1 | 1/2003 | Vo et al. |
| 2006/0190075 | A1 | 8/2006 | Jordan et al. |

* cited by examiner

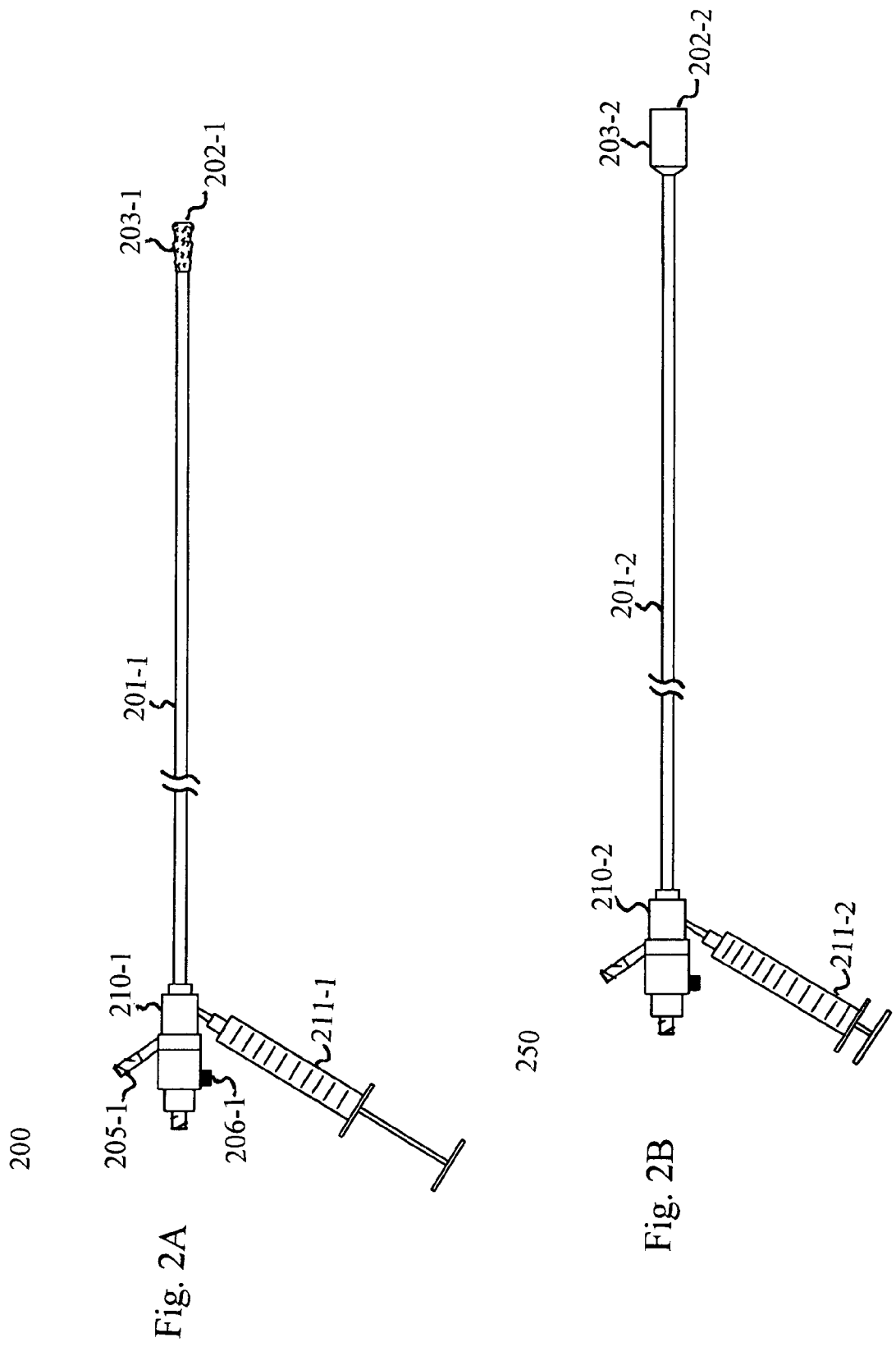

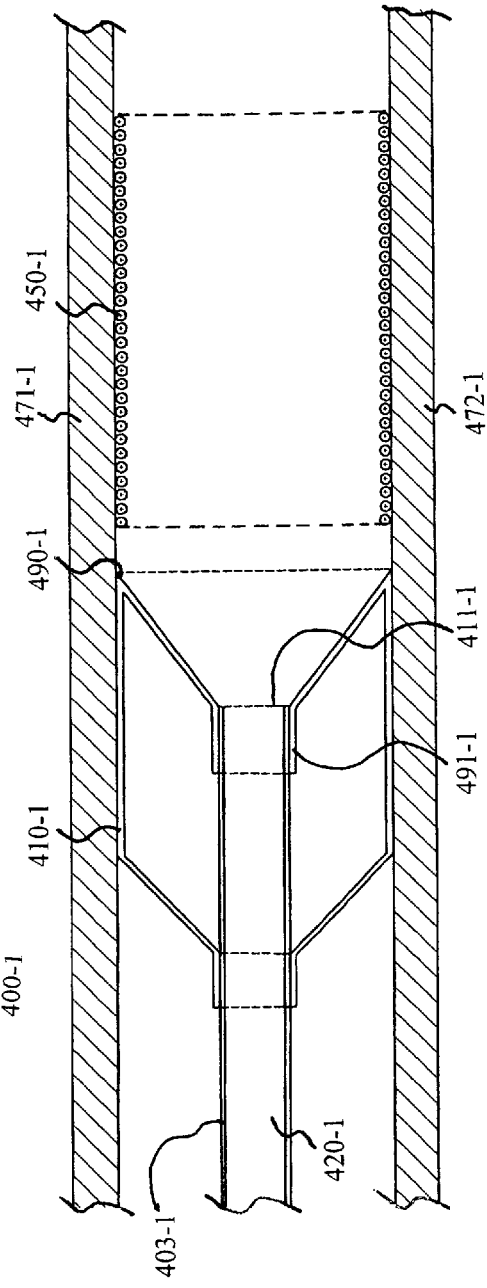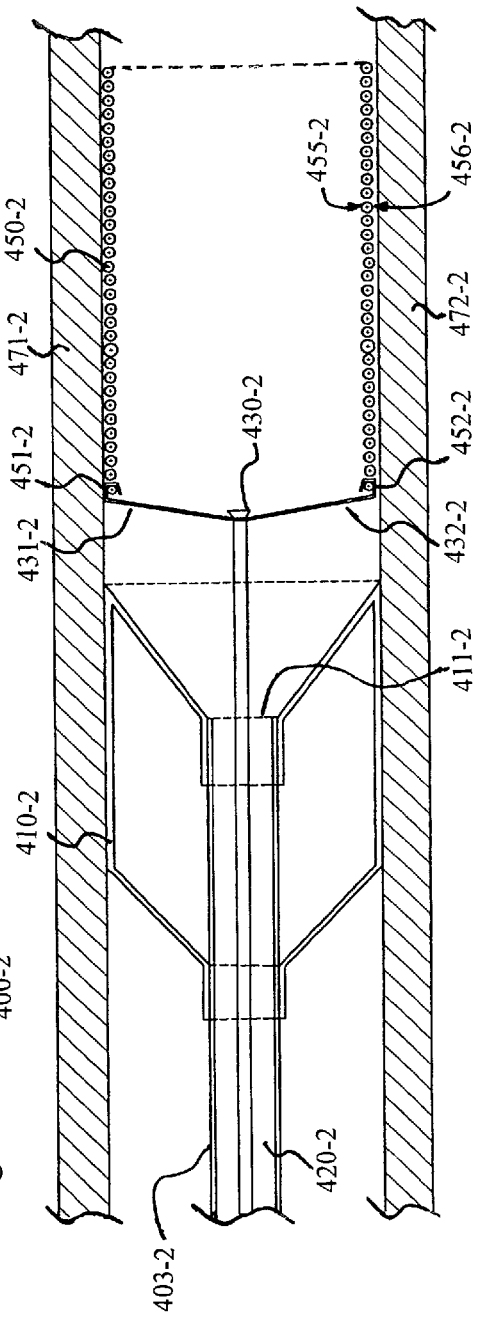

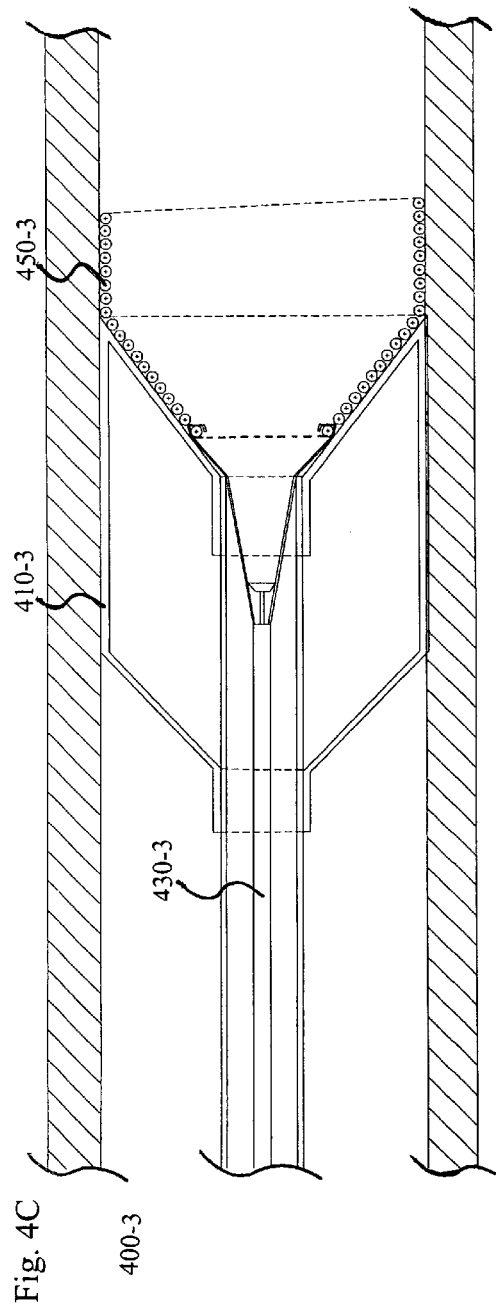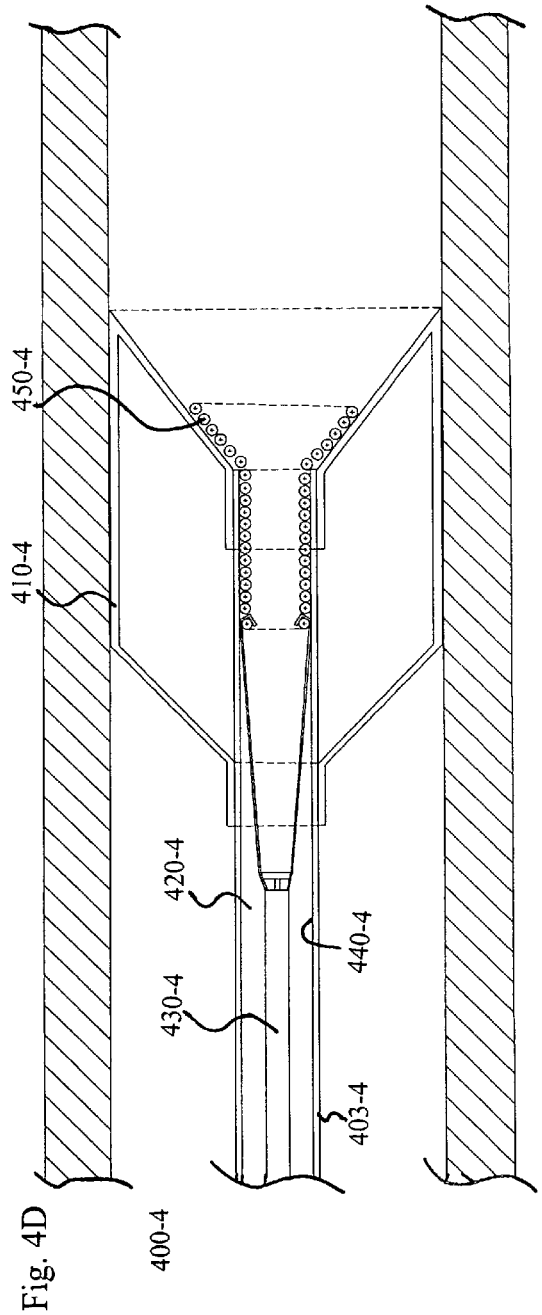

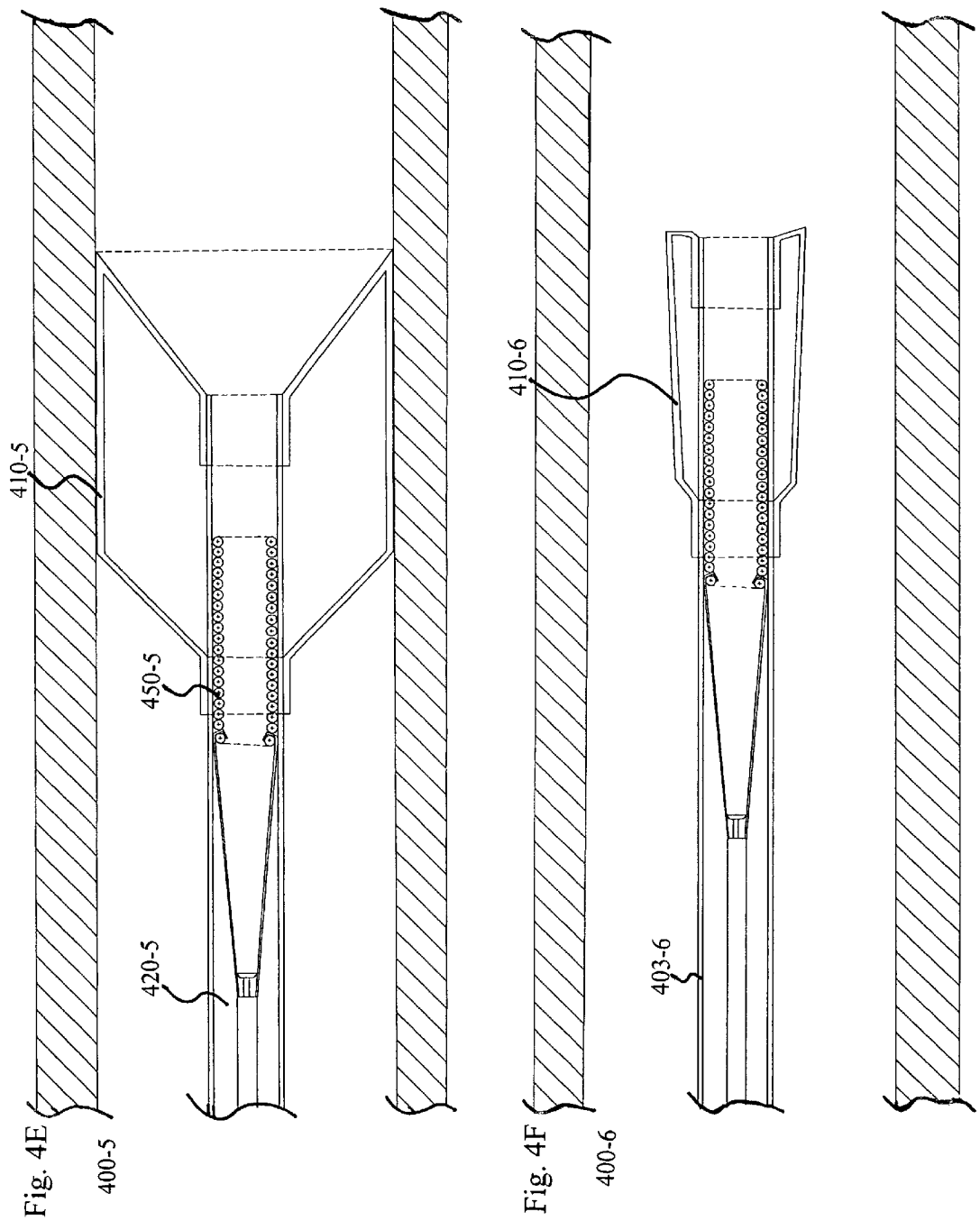

STENT AND OTHER OBJECT REMOVAL FROM A BODY

PRIORITY

This patent application claims priority to, and is a continuation of, U.S. Pat. No. 8,038,704 titled STENT AND OTHER OBJECT REMOVAL FROM A BODY, filed on Jul. 27, 2005, which is herein incorporated by reference.

BACKGROUND

In the field of medical devices, stents can be used to provide health benefits in human bodies. In some embodiments, a stent can beneficially support anatomical structures in a human body. In some embodiments, a stent can also contain and/or deliver beneficial substances to a human body, such as chemicals and/or drugs. A stent is a physical structure, which can form one or more passageways. In various embodiments, a stent can be coated with one or more beneficial substances, such as active chemicals or drugs. A stent can be placed in various anatomical pathways in a human body, such as blood pathways, air pathways, and waste pathways. A stent can also be placed in various ducts or other anatomical structures in a human body.

Although a stent is placed in a human body to provide health benefits, in some instances, a stent can cause undesirable effects on that body and/or prove to be inadequate to provide the health benefits intended. For example, a stent can fail to provide its intended health benefits to the body in which it is placed. A physical structure of a stent, such as a strut, can malfunction, break, or fail. A beneficial coating on a stent can exhaust or expire. A stent can be in an incorrect location in a human body. A stent can cause various harmful effects in the body in which it is placed. Thus, in some instances, it can be desirable to remove a stent that has been placed in a human body.

BRIEF SUMMARY OF THE INVENTION

Embodiments concern removal of an object from a body with a deployable receiving socket. dr

BRIEF DESCRIPTION OF THE DRAWINGS

FIG. 2A-28 illustrates embodiments of the present disclosure suitable to remove objects from a body.

FIGS. 4A-4F illustrates embodiments of the present disclosure removing a stent from an anatomical pathway.

FIGS. 5A-58 shows block diagrams of embodiments of the present disclosure.

FIG. 6 illustrates a deployed receiving socket.

DETAILED DESCRIPTION

Figure 1A:
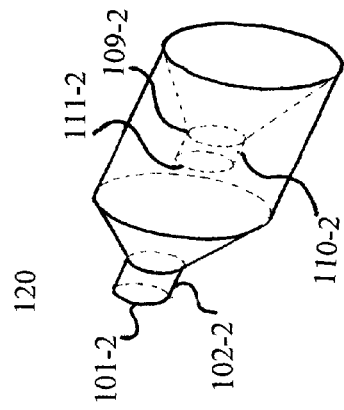
FIG. 1A-1D illustrates balloons suitable to implement embodiments of the present disclosure.

The present disclosure provides methods, devices, and systems for removing objects from inside a human body. In various embodiments of the present disclosure, a socket is deployed from a catheter, the socket being conically shaped and transitioning from an annularly shaped distal lip of the balloon to a lumen of the catheter. In various embodiments of the present disclosure, an inflatable balloon is provided on a distal end of a catheter, a surface of the balloon defining a socket inwardly sloped toward a lumen of the catheter. Various embodiments of the present disclosure also include attachment and manipulation tools for moving an object through the socket and into the lumen of the catheter. Various embodiments of the present disclosure also include reducing a diameter of a stent while the stent is moved through the socket.

Stents, as they are known in the art, include metal and plastic structures forming a single or multiple tubes. Various stents include matrices of thin wires woven, braided, or connected to define circular or elliptical tubes. Metal stents can be constructed of NiTi alloy or alloys of stainless steel, among other metals. Stents can also be covered with a polymeric material as disclosed by Goodwin, et al. (U.S. Pat. No. 6,808,533) or coated for purposes of containing and/or exuding a drug, as disclosed by Schaldach, et al. (U.S. Pat. No. 6,796,998).

Placement of stents in blood pathways includes placement in arteries. Placement of stents in air pathways includes placement in tracheal and bronchial airways. Placement of stents in waste pathways includes placement in the urethra. Stents can also be placed in various ducts and in locations to support surrounding anatomical systems and structures or deliver drugs, among other things. However, placement of stents, as well as other objects, in the body is not so limited.

Many circumstances can lead to a desire to remove a stent or another object that has been placed within a body. Many circumstances can also lead to a desire to remove biological material from a body. Stents, while being placed, or after placement, can cause undesirable effects harmful to the body in which it is located. Such harmful effects can be caused by normal function, abnormal function, or malfunction of the stent and/or the delivery system or other part or device used within the body. Stents can collapse inward, fail to deploy as intended, and strain and/or break anatomical structures. Moreover, a stent may prove to be insufficient to adequately treat a problem that had instigated the delivery of a stent. Furthermore, tissues surrounding the stent may be harmed by the presence of the stent. An immune system of a body may attack a stent and its associated materials causing problems.

Balloons can be made from various polymers, as well as other materials. Polymeric balloons can be made from thermoplastic and/or thermoset materials. Many methods of balloon forming are known in the art. By way of example and not by way of limitation, balloons can be made by extruding polymeric material into tube form, the tube including a lumen. An extruded tube can be placed in a mold, an inside surface of the mold defining a negative of the exterior of a balloon. The lumen of the balloon can be pressurized and the mold can be heated, the heat transferring to the tube. By combination of the pressure and heat, the tube can expand outwardly to the inside surface of the mold. The mold can then be cooled, which in turn can cool the polymeric material. A variety of balloon shapes can be made by this and other balloon making processes. Additional balloon blowing tools and methods are herein incorporated by reference, as described by Mahoney, et al. (U.S. Pat. No. 6,863,856).

FIG. 1A illustrates an embodiment of a balloon. The balloon 100 includes a first opening 101-1, defined by the end of a first tail 102-1. A tail of a balloon, as used herein, refers to a sectional length of a balloon on an end of the balloon. Balloons can include two tails. The balloon 100 also includes a first seam 103-1, adjacent to a first transition section 104-1. An outer diameter of the first transition section 104-1 can be approximately equal to the outer diameter of the first tail 102-1 at the first seam 103-1. Between the first seam 103-1 and a second seam 105-1 the outer diameter of the first transition section can change along a sectional length of the balloon 100. In various embodiments, the respective outer surfaces of the first transition section 104-1 and the second transition section 108-1 can take the form of a cone, the cone not having a pointed end. In various embodiments of the present disclosure, different shapes are contemplated for transition sections 104-1 and 108-1, including but not limited to sections of cones. Moreover, various embodiments of the present disclosure can include only one transition section.

The balloon 100 can include a middle section 106-1, located between a second seam 105-1 and a third seam 107-1. The middle section 106-1 can have an approximately constant outer diameter along its sectional length, however, various embodiments of the present disclosure are not so limited. The balloon 100 can also include a second transition section 108-1. The outer diameter of the second transition section can change between the third seam 107-1 and a fourth seam 109-1. The balloon can also include a second tail 110-1, one end of which can define a second opening 111-1.

The embodiment of a balloon in FIG. 1A illustrates a balloon 100 that is substantially hollow. Balloons of different embodiments have various wall thicknesses. Wall thicknesses can range from 0.001" to 0.010" (0.0254 mm to 0.254 mm), but other wall thicknesses, including larger and smaller wall thickness than the dimensions given herein, are suitable depending on various configurations, including but not limited to the balloon material used. Moreover, in various embodiments of the present disclosure, the wall thickness of the balloon 100 can be different for different parts of the balloon 100. Thus, some portions, such as third seam 107-1, can have a wall thickness smaller than the second transition section 108-1, which in some embodiments could correspond to a flexible joint between the middle section 106-1 and the second transition section 108-1 and/or a reinforced second transition section 108-1 that is more resistant to tearing and/or punctures. Varying wall thickness in balloons can be accomplished by several processes, including dual stage balloon blowing (blowing different portions of the balloon at different times) and processing the material between blowing cycles, and/or using an extruded tube with varying wall thicknesses (whether the tube is extruded with a varying wall thickness or the extruded tube is necked after extrusion).

Reinforcement of balloon sections can also be accomplished by several processes. One process includes adhering one or more additional layers to the balloon material. This can be accomplished after a balloon is blown, by adhering a layer to the balloon with an adhesive agent, solvent, applied heat to weld the two materials together, or another process known in the art. In various embodiments of the present disclosure, layers can be added to the balloon wall by placing the additional layers within the balloon mold before the balloon is blown, such that the layers contact the balloon as the balloon is being blown and in the process attach to the balloon wall. Attachment in this way can be accomplished by heat bonding between the two materials, the heat provided by the heated mold in which the blowing balloon is placed. A reinforcement layer can be added to a part of or to an entire balloon surface. In various embodiments of the present disclosure, a reinforcement layer can be added to a portion of the second transition section 108-1, the first transition section 104-1, and/or the middle section 106-1. A layer added to a balloon can be a layer of polymeric material, and/or metal. Moreover, struts, wires, bars, tubes, and other parts can also be added to the balloon material and the various sections of a balloon in the same way that a layer is added, as discussed above.

Figure 1B:
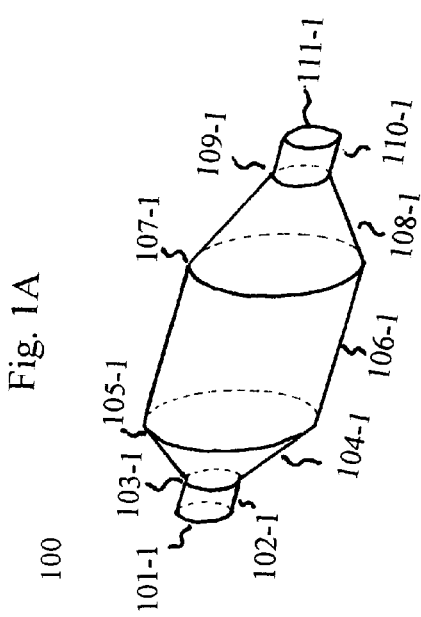

FIG. 1B illustrates an embodiment of a partially inverted balloon. The partially inverted balloon 120 can be formed from balloon 100 of FIG. 1A by inverting a portion of the balloon 100, but various processes for making a partially inverted balloon 120 are not so limited. By way of example and not by way of limitation, a second opening 111-1 of the balloon 100 of FIG. 1A can be turned inward, as if to be turned inside-out. This inversion can be continued to include the whole of the second tail 110-1, the fourth seam 109-1, and the second transition section 108-1, stopping at or before the third seam 107-1 of the balloon 100 of FIG. 1A. By way of example and not by way of limitation, the second tail 110-1 of the balloon 100 can become the second tail 110-2 of the partially inverted balloon 120. Also, the second opening 111-1 of the balloon 100 can become the second opening 111-2 of the partially inverted balloon 120, which in the embodiment illustrated in FIG. 1B opens to the inside of the inverted balloon 120.

Various embodiments of the present disclosure do not necessarily need a partially inverted balloon, or a balloon, to accomplish the same as a partially or wholly inverted balloon, such as partially inverted balloon 120. For example, a balloon could be blown with a suitable shape not needing inversion to accomplish the same as a partially inverted balloon. For example, a balloon can be blown which when mounted on a catheter includes a surface that defines a socket that is inwardly sloped toward a lumen of the catheter, the balloon not in an inverted configuration. Moreover, object and/or stent capture of the present disclosure can be accomplished without a balloon. For example, different materials can be employed to create shapes suitable to reduce the diameter of a stent such that the stent can be removed from an anatomical passageway.

Figure 1C:
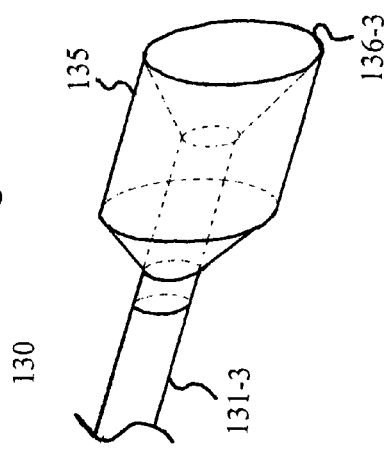

FIG. 1C illustrates an embodiment of a partially inverted balloon 135 mounted on a catheter shaft 131-3. Balloons can be mounted on catheter shafts in various ways. For example, a partially inverted balloon, such as the partially inverted balloon 120 of FIG. 1B, can be mounted on a catheter shaft 131. By way of example and not by way of limitation, the catheter shaft-partially inverted balloon assembly 130 of FIG. 1C can be made from the partially inverted balloon 120 of FIG. 1B by moving an end of a catheter shaft 131-3 through a first opening 101-2, through the first tail 102-2, and through the second opening 111-2. The end of the catheter shaft 131-3 can be moved past the forth seam 109-2, however, some embodiments of the present disclosure locate the end of the catheter shaft 131-3 between the second opening 111-2 and the forth seam 109-2.

In various embodiments of the present disclosure, the balloon 135 can include a surface that defines a socket that is inwardly sloped toward the catheter shaft 131-3, which can include a lumen. In various embodiments of the present disclosure, this inwardly sloped surface can correspond to a first transition section 104-1 or a second transition section 110-1 of the balloon 100 illustrated in FIG. 1A if the balloon 100 is partially inverted or processed. However, various embodiments of the present disclosure are not so limited.

In various embodiments of the present disclosure, a surface of the balloon 135 can define a funnel shaped cavity that transitions from an annularly shaped distal end of the balloon 135 to a lumen of a catheter shaft 131-3. In various embodiments of the present disclosure, this funnel shaped cavity defined by a surface can correspond to a first transition section 104-1 or a second transition section 110-1 of the balloon 100 illustrated in FIG. 1A if the balloon 100 is partially inverted or processed. However, various embodiments of the present disclosure are not so limited.

In various embodiments of the present disclosure, a surface of the balloon 135 can define a socket that is inwardly sloped toward a lumen of the catheter shaft 131-3. Furthermore, the surface defining the socket can include a section where the surface is linear, or substantially linear, that is, linear except for imperfections in the material and/or slight bowing from under or over inflation. By way of example and not by way of limitation, a substantially linear section of a surface can, in some embodiments, correspond to a first transition section 104-1 or a second transition section 110-1 of the balloon 100 illustrated in FIG. 1A if the balloon 100 is partially inverted or similarly processed. Furthermore, the socket can be conically shaped. As used herein, conically shaped refers to a shape that takes the form of all or part of a cone. By way of example and not by way of limitation, a surface that defines a socket that is conically shaped can take the form of a cone, or the negative of a cone, but does not include the pointed top. By way of example and not by way of limitation, a surface of a balloon can form a conical shape, including a socket, despite slight bowing in the sides due to under or over inflation and/or imperfections in the material.

In various embodiments of the present disclosure, the balloon 135 of FIG. 1C can include a surface that defines a socket inwardly sloped toward the catheter shaft 131-3 wherein the socket is conically shaped and the surface transitions from an annularly shaped lip 136-3 of the balloon 135 to an end of the catheter shaft 131-3. By way of example and not by way of limitation, the surface defining the conically shaped socket can, in some embodiments, correspond to the first transition section 104-1 or a second transition section 110-1 of the balloon 100 illustrated in FIG. 1A if the balloon 100 is partially inverted or similarly processed.

Figure 1D:
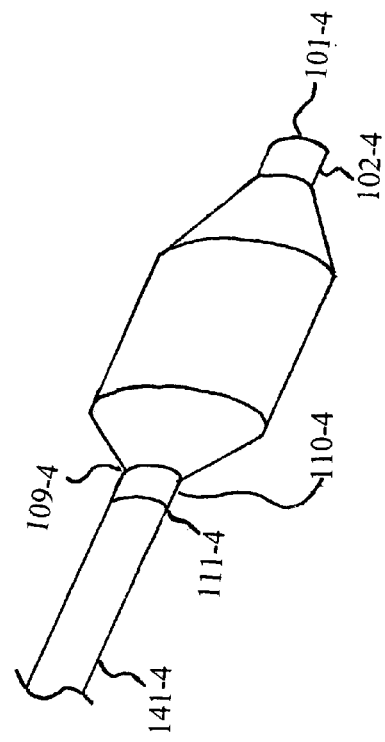

FIG. 1D illustrates an embodiment of a balloon being inverted while partially on a catheter shaft. In various embodiments of the present disclosure, the balloon of FIG. 1D can be the balloon 100 of FIG. 1A. By way of example and not by way of limitation, an end of a catheter shaft 141-4 can be moved through the second opening 111-4 and located between the forth seam 109-4 and the second opening 111-4, the second opening 111-4, and the forth seam 109-4 corresponding to the second opening 111-1 and the forth seam 109-1 of FIG. 1A, however, the present disclosure is not so limited. Next, the second tail 110-4 can be attached to the catheter shaft.

Attachment can be accomplished by various methods, including applying heat (generated by any source, including RF, and thermocouples) and/or pressure to the outer surface of the second tail 110-4. The second tail 110-4 can also be attached to the catheter shaft 141-4 by any other adhering means, including but not limited to, solvent bonding, adhesive bonding (including but not limited to use of epoxies and cyanoacrylates) and/or sonic welding.

Continuing with the non-limiting example presented in connection with FIG. 1D, once the second tail 110-4 is over the catheter shaft 141-4 the balloon material can be brought through the first opening 101-4 such that the first opening 101-4 and the first tail 102-4 are over the catheter shaft 141-4. In various embodiments of the present disclosure, the result of the balloon inversion shown in FIG. 1D can be the same as the result illustrated in FIG. 1C.

In various embodiments of the present disclosure, the inside of a balloon mounted on a catheter shaft can be isolated such that fluids and gasses between the balloon material and the catheter shaft cannot escape, nor can gasses or fluids outside of the volume between the balloon and the catheter shaft get within this volume once sealed, except by a valve and/or some inflation mechanism. By way of example and not by way of limitation, a section of a catheter shaft over which a balloon will be placed can be cut to tap into a second lumen of the catheter shaft, and this same lumen can be sealed on the distal end (such as by a heat seal or a plug of material), such that if gas and/or fluid was provided through the second lumen on the proximal end of the catheter shaft, a balloon mounted on the catheter shaft would inflate. Balloon tails and other parts can be attached and/or adhered to accomplish sealing, as discussed herein.

Balloons of the present disclosure can be made from a variety of polymers, polymer hybrids, as well as from other types of materials. Materials of various balloons of the present disclosure can have elastic or inelastic properties. Balloons can be made from compliant, semi-compliant, and/or non-compliant polymeric materials. In different embodiments of the present disclosure, different advantages can be sought by use of polymers with different properties. For example, some semi-compliant and non-compliant balloons, as they are known in the art, can retain a rigid shape once inflated. In contrast, compliant balloons will continue to increase in size the greater the pressure is produced within the balloon. In contrast, some semi-compliant and non-compliant balloons will take a shape once a certain pressure is provided, and greater pressure will not cause the inflated balloon to change shape other than slight bowing. This rigid shape can be useful because in some embodiments the rigidity of a semi-complaint or a non-compliant inflated balloon can resist deflection when a force is applied to the balloon. Thus, in some embodiments, a balloon formed from semi-compliant or non-compliant polymeric materials, mounted on a catheter shaft with a central lumen, can include a surface that defines a funnel shaped socket that is inwardly sloped toward the central lumen. By way of example and not by way of limitation, an object moved through the funnel shaped socket can apply force and torque to the balloon surface, but the balloon surface will not deflect and the structure defined by the inflated balloon will remain despite the applied force and torque, in-part because of the properties of the semi-complaint or non-compliant polymeric balloon material.

Moreover, semi-compliant and non-compliant balloons can form shapes that compliant balloons cannot, especially fine features, sharp edges, fine lips, and sharp ridges.

Polymeric material that can exhibit semi-compliant or non-compliant properties in certain configurations include, but are not limited to, poly(ethylene terphthalate), polyamides, polyimide, polyphenylene sulfides, thermoplastic polyimide, polyesters, polycarbonates, poly vinyl chloride, polypropylene and polyurethanes.

Semi-compliant and non-compliant balloon materials can be more brittle in some circumstances and in some circumstances harder to process as compared to compliant balloon materials. This is due in part to the inelastic properties that some semi-compliant and non-compliant materials exhibit in certain configurations. However, several techniques can be employed to allow semi-compliant and non-compliant materials to be processed as compliant materials, including temporarily changing the elastic properties of the material. For example, semi-compliant and non-compliant materials can be annealed before and/or after manipulation and processing. Also, the temperature at which semi-compliant and non-compliant materials are processed and manipulated can be increased and later lowered when the processing and manipulation is complete. In addition, the semi-compliant and non-compliant materials can be exposed to a diluted solvent, then processed and manipulated, then dried to remove the solution and the solvent. By these and other techniques that are known in the art, semi-compliant and non-compliant materials can be processed and manipulated, including temporarily imparting elastic properties to the materials, to take the desired form. Temporarily or permanently changing the elastic properties of a material can be useful for several purposes, including but not limited to, moving a tail of a balloon onto and/or over a catheter shaft, or over another object, wherein the balloon is made from a non-compliant material and an inner diameter of the balloon tail is smaller than an outer diameter of the catheter shaft at a resting state.

Catheters, as they are known in art, can include elongated tubes made from various materials, including polymers and metals. Catheters can have one or more lumens. Lumens, as they are known in the art, can include a passageway within a catheter that runs some distance of the catheter, and in some cases can run the entire length of the catheter, having an opening on each end. However, a lumen can also be closed, sealed, plugged, and/or transitioned into another feature, and thus in these ways, among other ways, lumens may not run the entire length of a catheter in all embodiments. Polymeric catheters, with one or more lumens, can be extruded, as is known in the art.

FIG. 2A illustrates an embodiment of the present disclosure. FIG. 2A shows a medical device 200. In the medical device 200 of FIG. 2A, an uninflated balloon 203-1 is mounted on a distal end 202-1 of a catheter shaft 201-1. An access and control assembly 210-1 is attached to the proximal end of the catheter shaft 201-1. In various embodiments, the access and control assembly 210-1 can provide access to one or more lumens of the catheter shaft, including but not limited to a central lumen and an inflation lumen. In various embodiments, the access and control assembly 210-1 can also provide an interface for electrical and mechanical devices, accessories, peripherals, luers, signals, fluids, and tools. The embodiment of the access and control assembly 210-1 illustrated includes a luer attachment 205-1 and conductor connection 206-1, but various embodiments of the present disclosure are not so limited.

Also shown in the embodiment illustrated in FIG. 2A is an inflation control device 211-1. The inflation control device 211-1 can be any means and/or mechanism known in the art for inflating balloons, providing fluids, and/or controlling pressure, including but not limited to syringes, plungers, and pumps. In various embodiments of the present disclosure, the inflation control device 211-1 can be in communication with an inflation lumen, the inflation lumen also in communication with the uninflated balloon 203-1, such that fluids provided by the inflation control device 211-1 can flow through the inflation lumen and into the uninflated balloon 203-1, however, various embodiments of the present disclosure are not so limited.

The embodiment shown in FIG. 2A can be employed in various ways to remove objects, including natural and artificial objects, from a body. The medical device 200 illustrated in FIG. 2A could be used to remove objects from various areas of the body, but is particularly suited to remove objects from anatomical passageways, including but limited to pathways of the circulatory system, pathways of the respiratory system, and pathways of the digestive and gastrointestinal system. By way of example and not by way of limitation, the distal end 202-1 of the medical device 200 can be feed through an incision in a femoral artery and run over a guide wire to a vasculature associated with the heart, such as a coronary artery. In this non-limiting example, the uninflated balloon 203-1 can be located proximal to an object, such as a stent that has previously been deployed in the coronary artery. The uninflated balloon 203-1 can then be inflated by inflation means 211-1. However, various embodiments of the present disclosure are not so limited.

Embodiments of the present disclosure can be introduced into a body by various methods. By way of example and not be way of limitation, a portion of the medical device 200 can be inserted through the mouth to access objects in the throat, esophageal, trachea, bronchia, and stomach areas, as well as other areas of the body. In various embodiments of the present disclosure, a portion of the medical device 200 can be introduced into the circulatory system of a body and navigated through the pathways therein. Thus, access can be gained to coronary arties through a hole in the femoral artery, wherein the medical device 200 is routed to the arteries of the heart. Introduction, navigation, and use of the medical device 200, as well as in other embodiments of the present disclosure, can be aided by use of an introducer. Embodiments of the present disclosure can also employ any methods and/or devices, as are known in the art, for introduction and use within the body.

FIG. 2B illustrates an embodiment of the present disclosure. FIG. 2B shows an inflated medical device 250. The result of inflation is illustrated in FIG. 2B, as the inflated medical device 250. In various embodiments of the present disclosure before, during, and/or after inflation, tools, wires, scopes, fluids, and/or signals can be introduced through, or accessed from, the access and control assembly 210-1 and 210-2. By way of example and not by way of limitation, the access and control assembly 210-2 can provide access to a central lumen of a catheter shaft 201-2, the central lumen extending to the distal end 202-2. Thus, tools can be routed through the access and control assembly 210-2, through the catheter shaft 201-2, past the inflated balloon 203-2, and through the distal end 202-2. A gasket or other sealing means can be provided in the access and control assembly 210-2, or at other locations of the medical device 200 and/or of the inflated medical device 250, to prevent bodily fluids from escaping the body through the inflated medical device 250, while also allowing access for tools and other parts to the inside of the body. However, various embodiments of the present disclosure are not so limited.

Guide wires, known in the art, can assist in navigation and location in and through anatomical pathways. By way of example and not by way of limitation, the medical device 200 can be routed over a guide wire by inserting the guide wire into a distal opening of the central lumen 202-1 or into the access and control assembly 210-1. However, various embodiments of the present disclosure are not so limited. Various embodiments of the present disclosure can employ a deflecting tip and/or a shaft that can be turned and/or articulated to navigate through anatomical pathways. Moreover, various embodiments of the present disclosure can also contain marker bands, antennas and/or radio opaque materials, as well as other imaging and location tools known in the art, to assist with navigation and location. Also, MRI and other imaging and location systems can be used with various embodiments of the present disclosure.

In various embodiments of the present disclosure, the inflated balloon 203-2 can include a surface that defines a socket that is inwardly sloped toward a lumen of the catheter shaft 201-1. Furthermore, in various embodiments, the socket can be conically shaped and the surface can transition from an annularly shaped distal lip of the balloon to a lumen of the catheter shaft 201-1.

In various embodiments of the present disclosure, a surface of the balloon 203-2 can define a funnel shaped cavity that transitions from an annularly shaped distal end of the balloon 203-2 to a lumen of a catheter shaft 201-2.

Figure 3A:
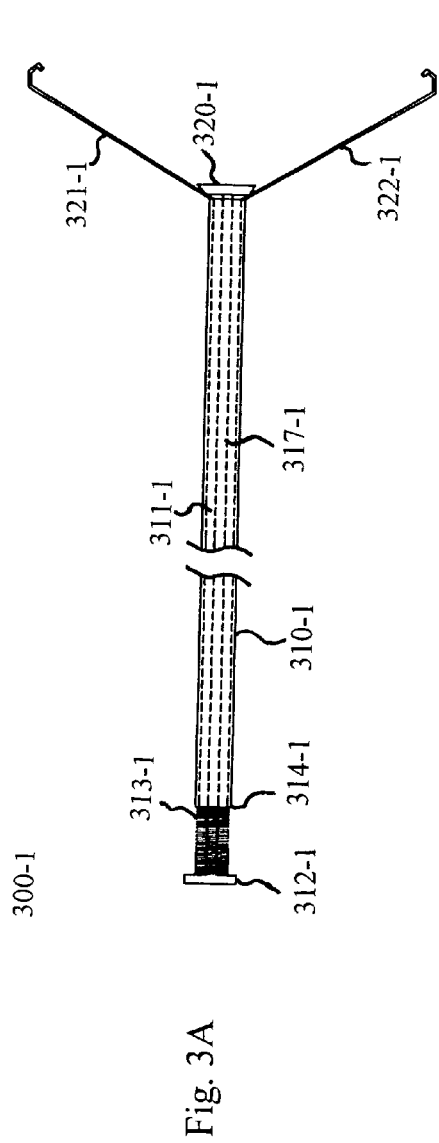
FIG. 3A-3C illustrates tools of the present disclosure.

FIG. 3A illustrates an embodiment of the present disclosure. FIG. 3A shows an attachment tool 300-1. In the embodiment shown in FIG. 3A, the attachment tool 300-1 includes a shaft 310-1 having a lumen 311-1, the lumen 311-1 accommodating a rod 317-1. By way of example and not by way of limitation, the rod 317-1 is attached to a plunger 312-1 and a head 320-1. The shaft 310-1 also includes a proximal end of the shaft 314-1. By way of example and not by way of limitation, arms 321-1 and 322-1 can be attached to the shaft 310-1. The embodiment of FIG. 3A also shows a spring 313-1 on the attachment tool 300-1. In the embodiment shown in FIG. 3A, the rod 317-1 runs through the center of the spring 313-1. Depending on the properties of the spring 313-1, the spring 313-1 can apply force to both the proximal end of the shaft 314-1 and the plunger 312-1. Thus, in various embodiments of the present disclosure, increasing the distance between the proximal end of the shaft 314-1 and the plunger 312-1 can cause the head 320-1 to push the arms 321-1 and 322-1 outward, in a deployed position.

In various embodiments of the present disclosure, attachment tool 300-1 can include any number of arms, such as arms 321-1 and 322-1. Although two arms are illustrated in the embodiment shown in FIG. 3A, various embodiments can include four, six, or any number of arms. Arms can be configured in various ways. For example, an attachment tool with four arms can have the four arms arranged ninety degrees apart, each attached to the distal end of the shaft 310-1. However, various attachment tools of the present disclosure are not so limited.

Figure 3B:
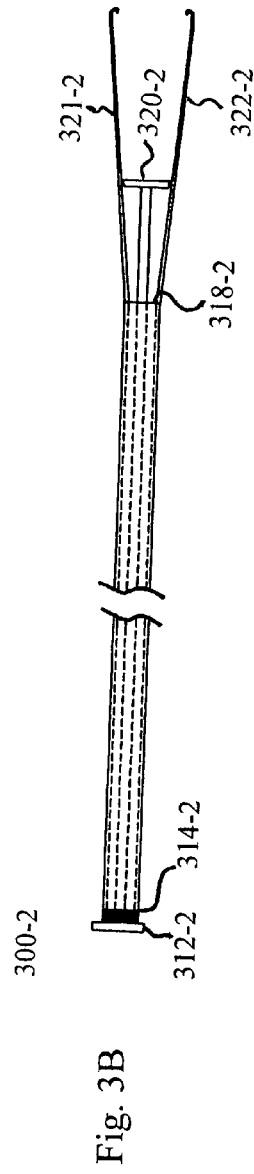

FIG. 3B illustrates an embodiment of the present disclosure. FIG. 3B shows an attachment tool 300-2. In the embodiment shown in FIG. 3B, the distance between a distal end of the shaft 314-2 and a plunger 312-2 has been reduced relative to the embodiment of the attachment tool 300-1 illustrated in FIG. 3A. Thus, a head 320-2 has moved away from the distal end of the shaft 318-2, relieving pressure on the arms 321-2 and 322-2, allowing the arms 321-2 and 322-2 to straighten in a undeployed configuration. In various embodiments of the present disclosure, in an undeployed configuration, a profile of the distal end of the attachment tool 300-2 is reduced, allowing the attachment tool 300-2 to fit and navigate through smaller spaces, such as a lumen of a catheter, as compared to an attachment tool 300-1 in a deployed position. However, various attachment tools of the present disclosure are not so limited.

Figure 3C:
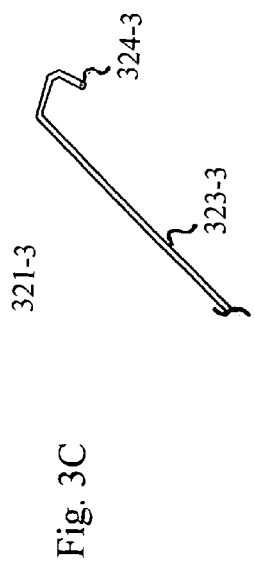

FIG. 3C illustrates an embodiment of the present disclosure. FIG. 3C shows a view of arm 321-3, and in some embodiments can resemble attachment arm 321-2 or 321-1. In the embodiment shown in FIG. 3B, the shaft 323-3 of arm 321-3 is connected to a hook 324-3. In various embodiments of the present disclosure, the hook 324-3 can accommodate, catch, latch onto, or hook a strut or a part of a stent, or a part of an object.

Various ends of arms 321-2 and 322-2 are contemplated in the present disclosure, and are not limited to the hook 324-3 as shown in 3C. In various embodiments, any method or means includes but is not limited to hooking, grasping, latching, catching, attaching and clasping onto an object. For example, the hook 324-3 can be replaced with an articulated clasp. In various embodiments, an arm of an attachment tool can include an adhesive to attach to an object. In various embodiments, an attachment tool can thread material, such as nylon, such that the material attaches to a stent or some other object. In various embodiments, a magnetic tool can also act on an object and/or a stent. However, various embodiments of the present disclosure are not so limited.

FIG. 4A illustrates an embodiment of the present disclosure in a cut-away view. FIG. 4A shows a distal end of a stent capture device 400-1. In the embodiment shown in FIG. 4A, the distal end of the stent capture device 400-1 has been located proximal to a stent 450-1, both the distal end of the stent capture device 400-1 and the stent 450-1 are located within arterial walls 471-1 and 472-1. A balloon 410-1, attached to a shaft 403-1, is shown as inflated. An inflation lumen, not shown, can be located within the walls of a shaft 403-1 to provide fluids to inflate the balloon 410-1. In various embodiments of the present disclosure, the distal end of the stent capture device 400-1 can be navigated to a location proximal to a stent 450-1 with an uninflated balloon, then when positioned, the balloon can be inflated. Balloons can be inflated to various diameters in different embodiments of the present disclosure. For example, an outer surface of the balloon 410-1 can be inflated to an outer diameter that is larger than an inner diameter of the arterial walls 471-1 and 472-1 before the inflation of the balloon 410-1. The outer diameter of an inflated balloon being larger than the inner diameter of arterial walls, thus increasing the inner diameter of the arterial walls, can serve multiple purposes, including but not limited to anchoring and/or stabilizing the distal end of the stent capture device 400-1 and/or loosening the stent 450-1 from the arterials walls 471-1 and 472-1. In various embodiments of the present disclosure, the balloon 410-1 is made from non-compliant polymeric materials.

In various embodiments of the present disclosure, a balloon 410-1 can include a surface that defines a socket that is inwardly sloped toward a central lumen 420-1. This surface can be, in various embodiments, the surface of the balloon 410-1 between an annularly shaped lip 490-1, or a plane formed by the annularly shaped lip 490-1, and a distal opening 411-1 of the central lumen 420-1, or a plane formed by the distal opening 411-1 of the central lumen 420-1. In the embodiment shown in FIG. 4A, the surface of the balloon 410-1 is linear between the annularly shaped lip 490-1 and the distal opening 411-1 of the central lumen 420-1, however, various embodiments of the present disclosure are not so limited. In various embodiments of the present disclosure, this inwardly sloped surface can correspond to the first transition section 104-1 or a second transition section 110-1 of the balloon 100 illustrated in FIG. 1A if the balloon 100 is partially inverted or processed.

In various embodiments of the present disclosure, a balloon 410-1 can include a surface that defines a socket that is inwardly sloped toward a central lumen 420-1. This surface can be, in various embodiments, the surface of the balloon 410-1 between an annularly shaped lip 490-1, or a plane formed by the annularly shaped lip 490-1, and a distal opening 411-1 of the central lumen 420-1, or a plane formed by the distal opening 411-1 of the central lumen 420-1. In various embodiments of the present disclosure, this socket can be conically shaped between the annularly shaped lip 490-1 and the distal opening 411-1 of the central lumen 420-1, or the respective planes formed by each.

In various embodiments of the present disclosure, various parts and sockets can have specific and/or relative dimensions. By way of example and not by way of limitation, the distance between a distal opening 411-1 of the central lumen 420-1 and an annularly shaped lip 490-1, or the distance between the corresponding planes formed by each, can be greater than or less than other dimensions of the stent capture device 400-1, including but not limited to an outer diameter of the balloon 410-1 when the balloon 410-1 is inflated, an inner diameter of the central lumen 420-1, an outer diameter of the shaft 403-1, a length of a surface of the balloon 410-1 when inflated, or a distance between tails of the balloon 410-1. Other dimensions identified herein, as well as dimensions not identified, can include relative dimension requirements with respect to each other, such as a requirement that a diameter of an annularly shaped lip 490-1 of the balloon 410-1 when inflated be three times greater than an outer diameter of the shaft 403-1. However, various embodiments of the present disclosure are not so limited.

As shown in FIG. 4A, a balloon tail 491-1 of balloon 410-1 is contacting a surface of the shaft 403-1. The tail 491-1, as well as other parts of the balloon 410-1, can be attached to the shaft 403-1 by thermal weld, adhesive, solvent, and/or pressure, among others. The tail 491-1 can alternatively be attached to an inside surface of the central lumen 420-1. The balloon 410-1 and/or the shaft 403-1 can be shaped, processed, or modified to make a smooth surface transition from the balloon 410-1 to the shaft 403-1, including adding material and/or adding a fillet. Thus, in various embodiments, a seamless transition can be experienced by an object, such as a stent, moving through a socket formed by an inwardly sloped surface of the balloon 410-1 and into the central lumen 420-1.

FIG. 4B illustrates an embodiment of the present disclosure in a cut-away view. FIG. 4B shows a distal end of a stent capture device 400-2. In the embodiment shown in FIG. 4B, continuing from the non-limiting example presented in relation to FIG. 4A, an attachment tool 430-2 can been introduced, and routed through a central lumen 420-2 and a distal opening 411-2 of a shaft 403-2. The attachment tool 430-2 can be deployed and arms 431-2 and 432-2 can each hook stent struts 451-2 and 452-2, respectively. The attachment tool illustrated in FIG. 4B can include embodiments of the attachment tools illustrated in FIGS. 3A-3C, however, various embodiments of the present disclosure are not so limited. In various embodiments of the present disclosure, different attachment means can attach to a stent and/or other objects in different modes. By way of example and not by way of limitation, in the embodiment illustrated in FIG. 4B, the arms 431-2 and 432-2 of the attachment tool 430-2 can be moved between the stent 450-2 and the arterial walls 471-2 and 472-2 by first deploying the arms 431-2 and 432-2, pushing the attachment tool 430-2 in the distal direction, and then pulling the attachment tool 430-2 in the proximal direction such that the hooks set in struts of the stent 450-2 from the outside of the stent. In various embodiments of the present disclosure, articulating clasping means can be provided on the ends of arms 431-2 and 432-2 and can attach to struts 451-2 and 452-2 without dragging over the stent 450-2, or hooks orientated in a different way could be dragged along a inside surface 455-2 of the stent 450-2 to set in stent struts 451-2 and 452-2 from the inside of the stent, as opposed to dragging along a outside surface 456-2 of the stent, as explained above. These and other means and mechanisms are contemplated in the present disclosure for controlling and/or moving a stent, however, various embodiments of the present disclosure are not so limited.

The central lumen 420-2 of the stent capture device 400-2 can serve multiple functions, including accommodating scopes, signal conductors, guide wires, tools, attachment tools, navigation tools, imaging tools, and nets, among other things. Moreover, the central lumen 420-2 can accommodate captured objects and tissues. For example, stents can be drawn into the central lumen 420-2 for removal from the body. Also, the central lumen 420-2 can allow fluid flow within the shaft 403-2, including bodily fluids such as blood, which can be particularly useful for allowing blood to flow through an anatomical pathway even when a balloon is deployed in the pathway. This can be aided by porting in the shaft 403-2. However, various embodiments of the present disclosure are not so limited.

FIG. 4C illustrates an embodiment of the present disclosure in a cut-away view. FIG. 4C shows a distal end of a stent capture device 400-3. In the embodiment shown in FIG. 4C, continuing from the non-limiting example presented in relation to FIG. 4B, the distance between the stent 450-3 and distal end of stent capture device 400-3 can been closed, by either advancing the distal end of stent capture device 400-3 toward the stent 450-3 or by pulling the stent 450-3 toward and into the distal end of stent capture device 400-3 with the attachment tool 430-3, or by a combination of the two, such that the stent 450-3 is drawn into a socket defined by a surface of the balloon 410-3. As illustrated in FIG. 4C, the outer diameter of the stent 450-3 can reduced as the stent 450-3 is moved along a surface of the balloon 410-3. Thus, an outer profile, such as the outer diameter of a stent, can be reduced by moving the stent along a surface, the surface defining a socket inwardly sloped. Thus, the stent 450-3 can be reduced in diameter by moving the stent 450-3 through a socket defined by a surface of the balloon 410-3 causing relative movement between the stent and the socket. However, various embodiments of the present disclosure are not so limited.

This reduction in diameter can happen in a controlled way or in a non-controlled fashion. By way of example and not by way of limitation, the struts of the stent 450-3 can compact uniformly, or the struts of stent 450-3 can compact in a non-uniform manner. Moreover, the stent 450-3 can collapse inward, where the stent 450-3 no longer resembles a circle or has outer curved surfaces. Furthermore, the stent 450-3 can even break, including but not limited to strut fracture, bending, unbraiding and/or unweaving. In any case, any reduction in any profile and/or dimension of the stent 450-3 is contemplated in the present disclosure, including breaking of the stent 450-3.

FIG. 4D illustrates an embodiment of the present disclosure in a cut-away view. FIG. 4D shows a distal end of a stent capture device 400-4. In the embodiment shown in FIG. 4D, continuing from the non-limiting example presented in relation to FIG. 4C, a stent 450-4 can be drawn into a central lumen 420-4 of the stent capture device 400-4. By way of example and not by way of limitation, the stent 450-4 can be pulled further into the stent capture device 400-4 by attachment tool 430-4. In various embodiments of the present disclosure, the stent 450-4 can be reduced in diameter by moving the stent 450-4 through a socket defined by a surface of the balloon 410-4. By way of example and not by way of limitation, the central lumen 420-4 can be defined by an inner surface 440-4 of the catheter shaft 403-4. In various embodiments, the central lumen 420-4 can include a consistent inner diameter along its length, or its inner diameter can change along its length. Moreover, in various embodiments, the central lumen 420-4 can contain coatings or materials different from materials of the shaft 403-4.

FIG. 4E illustrates an embodiment of the present disclosure in a cut-away view. FIG. 4E shows a distal end of a stent capture device 400-5. In the embodiment shown in FIG. 4E, continuing from the non-limiting example presented in relation to FIG. 4D, a stent 450-5 can be contained within the central lumen 420-5 of the stent capture device 400-5. In various embodiments, once the balloon 410-5 is deflated, but not necessarily limited to a deflated condition, the stent 450-5 can be removed from a body by removing the stent capture device 400-5.

FIG. 4F illustrates an embodiment of the present disclosure in a cut-away view. FIG. 4F shows a distal end of a stent capture device 400-6. In the embodiment shown if FIG. 4F, continuing from the non-limiting example presented in relation to FIG. 4E, the balloon 410-6 is partially deflated. In various embodiments, the stent capture device 400-6 can have a smaller profile, including a smaller outer diameter, after the balloon 410-6 has been deflated. However, various embodiments of the present disclosure are not so limited. In various embodiments of the present disclosure, a sheath on the shaft 403-6 can be slid over the balloon 410-6, which can reduce the profile of the balloon 410-6 and/or insulate the balloon 410-6.

As illustrated in FIGS. 4A-4E, the outer diameter of the inflated balloon 410 is greater than the outer diameter of the shaft 403. In some embodiments of the present disclosure, this can allow a stent capture device 400 to navigate through pathways that are narrower than the balloon 410 when inflated. Also, in various embodiments, once a balloon 410 is inflated, a stent capture device can capture a stent 450 that is larger in diameter than the shaft 403 by moving the stent 450 into the central lumen 420-5, even though the stent 450 had a larger outer profile than the inner diameter of the central lumen 420-5, as illustrated in FIGS. 4A-4E. Moreover, in various embodiments, once the stent 450 has been partially or wholly contained within the stent capture device 400, the balloon 410 can be deflated and the stent capture device 400 and the stent 450 can be removed from the anatomical pathway. By way of example and not by way of limitation, in deflating a balloon 410, a profile of a stent capture device 400 can be decreased, allowing the stent capture device 400 to be withdrawn easily and removed from the body. However, various embodiments of the present disclosure are not so limited.

In various embodiments of the present disclosure, components can be coated or treated to change the properties of the components. For example, a surface of a balloon can be coated to provide hydrophilic or hydrophobic properties. Also, components, such as a balloon, can be coated to alter the coefficient of friction between the surface of the balloon and another material. Also, components can be coated and/or processed to change the lubriciousness of the components.

In various embodiments of the present disclosure, a port can be made in a catheter shaft, the port allowing fluid to flow from the outside of the catheter shaft, through the port and into a lumen of the catheter. Referring to FIG. 4B, a port can be made in the shaft 403-2, proximal to the balloon 410-2, for example. Thus, in this embodiment, fluid, such as blood, can flow from the proximal side of the balloon 410-2, into the central lumen 420-2, and through the distal opening 411-2 of the central lumen 420-2. In this configuration, blood, and/or other fluids, can flow in the anatomical passageway even when the balloon 410-2 is inflated. However, various embodiments of the present disclosure are not so limited.

Embodiments of the present disclosure can also include use of a sheath over a catheter shaft and over deployable components, including an uninflated balloon. In various embodiments, a sheath slid over a balloon can reduce the profile of a balloon, force fluid out of the balloon, and insulate the balloon, among other things.

Various embodiments of the present disclosure include attaching a balloon tail to the inside of a lumen of a catheter, and thus attachment of balloons is not limited to outer surfaces of a catheter or catheter shaft. In various embodiments of the present disclosure, a smoother transition between a catheter lumen and a surface of an inflated balloon defining a socket inwardly sloped toward the lumen can be formed, as compared to various embodiments where balloon tails are only attached to the outer surfaces of a catheter shaft.

Figure 6:
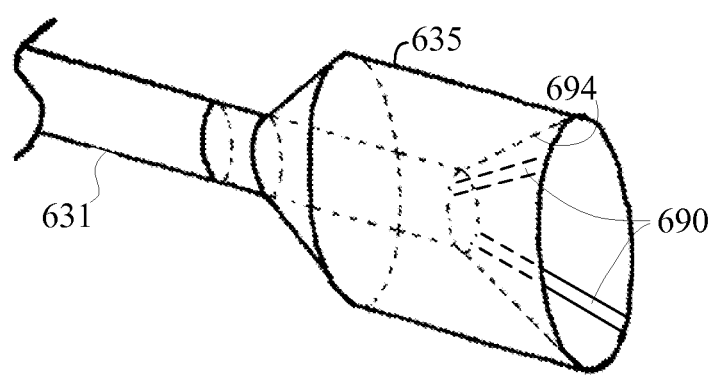

Different embodiments of the present disclosure can include a deployable receiving socket. A deployable receiving socket can include a balloon, but the present disclosure is not so limited. For example, the deployable receiving socket can include metal or polymer arms, each arm connected by mesh or other flexible material configuration and the proximal end of each arm can be attached to a catheter, the catheter including a lumen. The mesh could be made from metal or polymers, and the flexible material can include but is not limited to a polymer sheet. By way of example and not by way of limitation, in an undeployed position, the polymer layer and/or mesh can be folded under and/or in-between the arms. In various embodiments, when in a deployed position, the arms can hinge at their proximal ends while the distal end of each arm projects outward, unfolding the mesh or polymer sheet between the arms and forming a receiving socket that is sloped inwardly towards a lumen of the catheter. As an example, FIG. 6 illustrates a balloon 635 mounted on a catheter shaft 631, the balloon 635 deploying a receiving socket that comprises a plurality of arms 690 connected with flexible material 694, the flexible material 694 attached to the balloon 635.

In each of the embodiments illustrated in FIGS. 4A-4F, the balloon 410 can be made and formed from different materials and by different methods. In various embodiments, the balloon 410 can be a polymeric material, and/or multiple polymeric materials. By way of example and not by way of limitation, the balloon 410 can be made from a non-compliant polymeric material. By way of example and not by way of limitation, the balloon 410 can be made from a semi-compliant polymeric material. By way of example and not by way of limitation, the balloon 410 can be made from a compliant polymeric material. However, the present disclosure is not so limited.

The shape and configuration of the balloon 410 illustrated in each of FIGS. 4A-4E does not demonstrate all shapes and configurations contemplated within the present disclosure. For example, a surface of the balloon could define a socket that has a curved shape. By way of example and not by way of limitation, a balloon on a catheter shaft can include a surface that defines a socket with a curved shape inwardly sloped toward a lumen, wherein the curved shape resembles a power function, i.e. $y=x2$. Other shapes are also contemplated within the present disclosure.

Figure 5A:
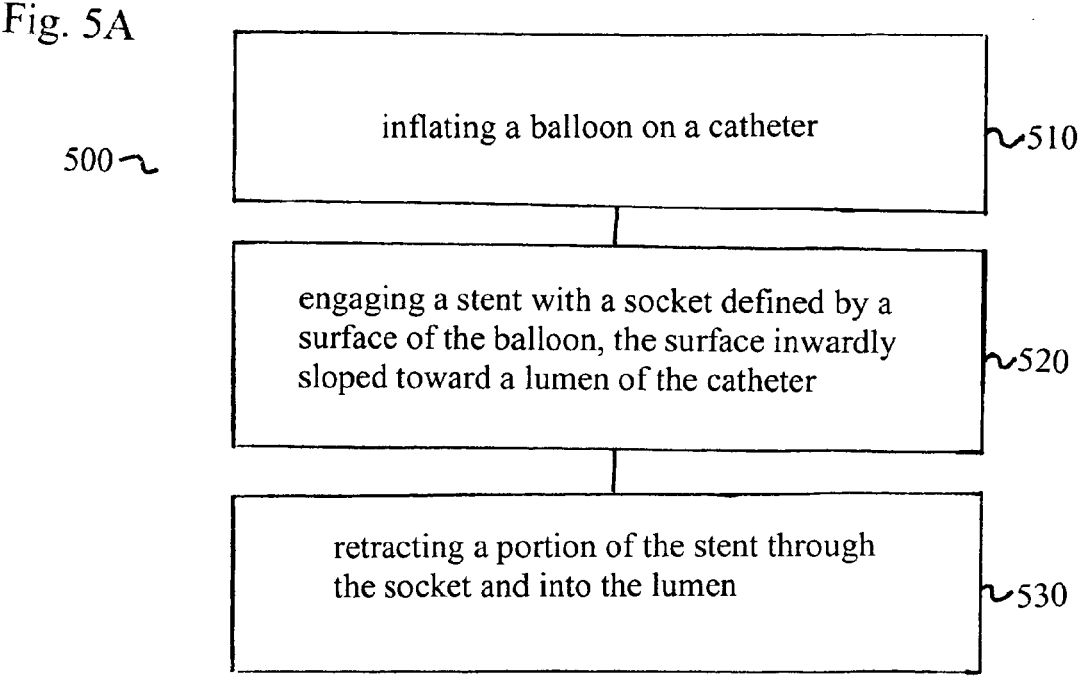

FIG. 5A shows a block diagram of an embodiment of the present disclosure. FIG. 5A is a block diagram representing a method for capturing a stent. In block 510, the method includes inflating a balloon on a catheter. In various embodiments of the present disclosure, the balloon can be attached to a distal end of the catheter. The catheter can also be introduced into an anatomical passageway of a body, such as an artery. The balloon can also be located proximal to an object in the body, including natural and/or artificial objects, such as a stent. A balloon inflated in connection with the method of block 510 can include an embodiment of a balloon from FIGS. 1A-1D, among others. In inflating the balloon, a surface of the balloon can define a socket that is inwardly sloped toward a lumen of the catheter. Inflating the balloon can also expand the inner diameter of the anatomical passageway by an outer surface of the balloon contacting the inner walls of the anatomical passageway. However, various embodiments of the present disclosure are not so limited.

In block 520, the method includes engaging a stent with a socket defined by a surface of the balloon, the surface inwardly sloped toward a lumen of the catheter. In various embodiments of the present disclosure, engaging a stent with a socket can include pulling the stent toward the inflated balloon and into the socket defined by a surface of the balloon. Engaging the stent with the socket of the balloon can include pulling the stent toward the socket with a tool, such as an attachment tool. However, various embodiments of the present disclosure are not so limited.

In block 530, the method includes retracting a portion of the stent through the socket and into the lumen. In various embodiments of the present disclosure, retracting a portion of the stent through the socket can include reducing a profile of the stent as the stent is moved through the socket defined by a surface of the balloon. In various embodiments, the stent can be retracted through the socket and into the lumen by using an attachment tool, such as the embodiments shown in FIGS. 3A-3C. However, various embodiments of the present disclosure are not so limited.

Figure 5B:
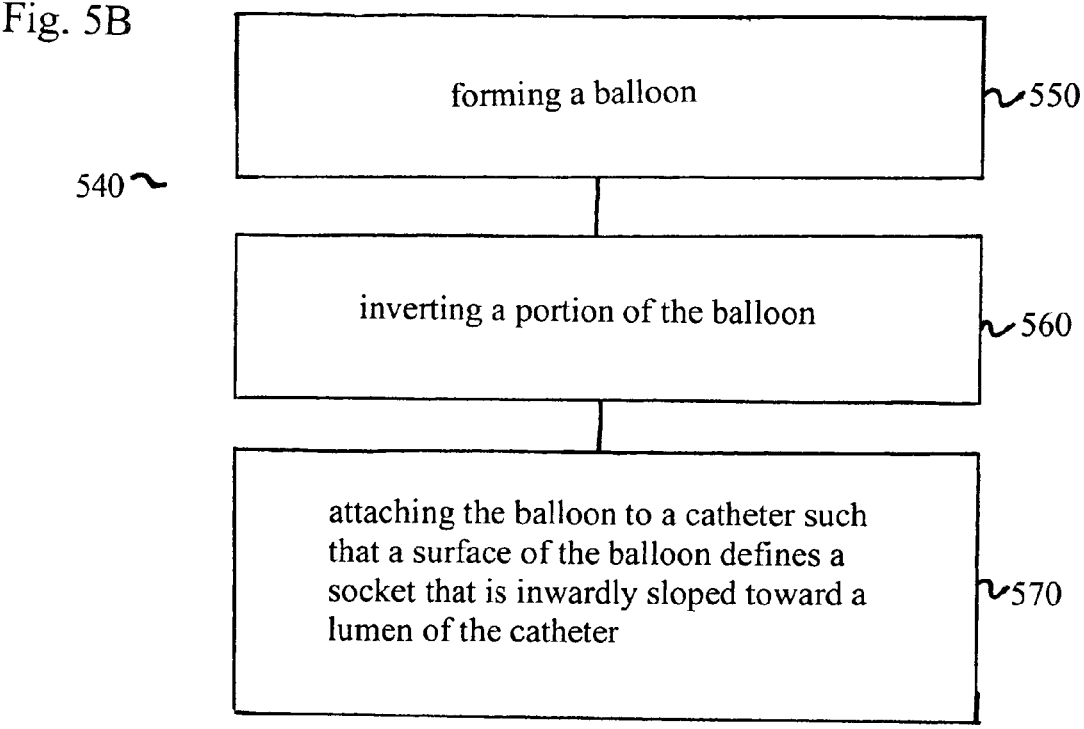

FIG. 5B shows a block diagram of an embodiment of the present disclosure. FIG. 5B is a block diagram representing a method for making a catheter. In block 550, the method includes forming a balloon. Forming a balloon can include blow molding a balloon, however the present disclosure is not so limited.

In block 560, the method includes inverting a portion of the balloon. In various embodiments, inverting can include turning a portion of the balloon inside-out, such that a surface of the balloon that was an outside surface of the balloon becomes an outside surface. Embodiments of balloons, before and after inversion, are shown in FIGS. 1A-1D, however, various embodiments of the present disclosure are not so limited. Inversion of a portion of the balloon can be done before the balloon is placed on the catheter, and/or after a portion of the balloon, such as a tail section, has been attached or placed on a catheter shaft. However, the present disclosure is not so limited.

In block 570, the method includes attaching the balloon to a catheter such that a surface of the balloon defines a socket that is inwardly sloped toward a lumen of the catheter. The inwardly sloped socket, as discussed herein, can include configuring the balloon such that the socket is conically shaped and the surface transitions from an annularly shaped distal lip of the balloon to a distal opening of the lumen. Attaching can include placing a tail of the balloon over the catheter shaft, and/or fusing one or more tails of the balloon to the catheter or catheter shaft, such as by heat fusing, applying an adhesive agent, applying a solvent, or other means for attachment known in the art. The balloon can be attached to the catheter such that a lumen of the catheter defines a passageway that is continuous with the surface that defines the socket. However, various embodiments of the present disclosure are not so limited.

In various embodiments, the profile of the stent can include an outer diameter of the stent. In various embodiments, a surface of the balloon that defines the socket can transition into the lumen of the catheter. Thus, a stent can be drawn, partially or wholly, into the lumen of the catheter. Once the stent is partially or wholly in the lumen, the catheter and the stent within the lumen can be removed from the body. However, various embodiments of the present disclosure are not so limited.

Although specific embodiments have been illustrated and described herein, it will be appreciated from this disclosure that any arrangement calculated to achieve the same techniques can be substituted for the specific embodiments shown. This disclosure is intended to cover any and all adaptations or variations of various embodiments of the present disclosure.

It is to be understood that the above description has been made in an illustrative fashion, and not a restrictive one. Combination of the above embodiments, and other embodiments not specifically described herein will be apparent upon reviewing the above description.

The scope of the various embodiments of the present disclosure includes any other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted such that the embodiments of the present disclosure have to include more features than are expressly recited in each claim.

I claim:

1. A method for removal of an object located within an anatomical pathway of a blood circulatory system of a body with a catheter, the method comprising:
    introducing a distal end of the catheter into the blood circulatory system in which the object is located, the catheter having a lumen with a distal opening;
    navigating the distal end of the catheter within the anatomical pathway to a location that is proximal of the location of the object;
    deploying a receiving socket on the distal end of the catheter, the receiving socket deployed by inflation of a balloon mounted on the catheter, the deployed receiving socket having a surface that is inwardly sloped toward the lumen, the deployed receiving socket comprising:
        a plurality of polymer arms, each polymer arm having a proximal end and a distal end, the proximal end of each polymer arm attached to the catheter, each polymer arm hinging at the proximal end while the distal end of each polymer arm projects outward upon deployment of the receiving socket; and
        flexible polymer material connecting the plurality of polymer arms, the flexible polymer material including a polymer sheet;
    engaging the object with the surface of the deployed receiving socket distally of the distal opening of the lumen, the object having an outer profile;
    moving the object through the deployed receiving socket and into the lumen such that the object is moved wholly into the lumen, the outer profile of the object being reduced distally of the distal opening as the object engages the surface of the deployed receiving socket and moves through the deployed receiving socket; and
    removing the object from the body within the lumen.

2. The method of claim 1, wherein moving the object through the deployed receiving socket and into the lumen further comprises moving the object with a tool, the tool extending within the lumen.

3. The method of claim 1, wherein the outer profile is larger than the inner diameter of the lumen before the object is moved through the deployed receiving socket and into the lumen.

4. The method of claim 1, wherein the object compacts as the object is moved through the deployed receiving socket.

5. The method of claim 1, wherein the flexible polymer material is attached to the balloon.

6. The method of claim 5, wherein the flexible polymer material is attached to the balloon as a layer on the balloon.

7. The method of claim 1, wherein the lumen defines a passageway that is continuous with the surface of the deployed receiving socket.

8. The method of claim 1, further comprising deflating the balloon to reduce an outer profile of the catheter to facilitate withdrawal of the catheter from the anatomical pathway.

9. The method of claim 1, wherein navigating the distal end of the catheter comprises running the catheter over a guide wire.

10. The method of claim 1, wherein the object is a stent.

11. The method of claim 1, wherein the object is an artificial object.

12. The method of claim 1, wherein the object is a natural object.

13. A method for removal of an object located within an anatomical pathway of a blood circulatory system of a body with a catheter, the method comprising:
- introducing a distal end of the catheter into the blood circulatory system in which the object is located, the catheter comprising a catheter shaft having a central lumen with a distal opening, the central lumen extending the entire length of the catheter shaft;
- navigating the distal end of the catheter within the anatomical pathway to a location that is proximal of the location of the object;
- inflating a balloon, the inflation of the balloon deploying a receiving socket on the distal end of the catheter, the deployed receiving socket having a surface that is inwardly sloped toward the central lumen, the balloon having a first tail mounted around the catheter shaft and attached to an outer surface of the catheter shaft and a second tail mounted around the catheter shaft distally of the first tail and attached to the outer surface of the catheter shaft, the balloon inflated through an inflation lumen;
- engaging the object with the surface of the deployed receiving socket distally of the distal opening of the central lumen of the catheter shaft;
- moving the object through the deployed receiving socket and into the central lumen, wherein the object is moved wholly into the central lumen and an outer profile of the object is reduced distally of the distal opening as the object engages the surface of the deployed receiving socket and moves through the deployed receiving socket; and
- removing the object from the body.

14. The method of claim 13, wherein the receiving socket comprises a plurality of polymer arms and flexible polymer material connecting the plurality of polymer arms, each polymer arm having a proximal end and a distal end, the proximal end of each polymer arm attached to the catheter shaft and the distal end of each polymer arm projecting outwardly as the receiving socket is deployed.

15. The method of claim 13, wherein moving the object through the deployed receiving socket and into the central lumen further comprises moving the object with a tool.

16. The method of claim 13, wherein the outer profile is larger than the inner diameter of the central lumen before the object is moved through the deployed receiving socket and into the central lumen.

17. The method of claim 13, wherein the object compacts as the object is moved through the deployed receiving socket.

18. The method of claim 14, wherein the flexible polymer material is attached to the balloon.

19. A method for removal of an object located within an anatomical pathway of a blood circulatory system of a body with a catheter, the method comprising:
- introducing a distal end of the catheter into the blood circulatory system in which the object is located, the catheter having a central lumen with a distal opening;
- navigating the distal end of the catheter within the anatomical pathway to a location that is proximal of the location of the object;
- deploying a receiving socket on the distal end of the catheter, the receiving socket deployed by inflation of a balloon mounted on the catheter, the deployed receiving socket having a surface that is inwardly sloped toward the central lumen, the deployed receiving socket comprising:
  - a plurality of polymer arms, each polymer arm having a proximal end and a distal end, the proximal end of each polymer arm attached to the catheter, each polymer arm hinging at the proximal end while the distal end of each polymer arm projects outward upon deployment of the receiving socket; and
  - flexible polymer material connecting the plurality of polymer arms, the flexible polymer material including a polymer sheet;
- engaging the object with the surface of the deployed receiving socket distally of the distal opening of the central lumen;
- moving the object through the deployed receiving socket and into the central lumen such that the object is moved wholly into the central lumen, the object moving along the surface of the deployed receiving socket distally of the distal opening as the object moves through the deployed receiving socket; and
- removing the object from the body.

20. The method of claim 19, wherein the flexible polymer material is attached to the balloon.

* * * * *